US007381305B2

(12) United States Patent
Zhu et al.

(10) Patent No.: US 7,381,305 B2
(45) Date of Patent: Jun. 3, 2008

(54) METHOD AND APPARATUS FOR MONITORING LIQUID AND SOLID CONTENTS IN A FROTH

(75) Inventors: JunYong Zhu, Madison, WI (US); Freya Tan, Madison, WI (US); Roland Gleisner, Jefferson, WI (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 474 days.

(21) Appl. No.: 11/090,537

(22) Filed: Mar. 25, 2005

(65) Prior Publication Data

US 2006/0213255 A1 Sep. 28, 2006

(51) Int. Cl.
*D21F 7/06* (2006.01)

(52) U.S. Cl. .................... 162/263; 162/198; 162/4; 162/5; 209/164; 209/166; 209/170

(58) Field of Classification Search ........... 162/263, 162/198, 4, 5; 209/164, 166, 170
See application file for complete search history.

(56) References Cited

U.S. PATENT DOCUMENTS

| | | | |
|---|---|---|---|
| 5,527,426 | A | 6/1996 | Marwah |
| 5,593,542 | A | 1/1997 | Wolfer |
| 5,714,040 | A | 2/1998 | Poy |
| 5,718,801 | A | 2/1998 | Li |
| 5,876,558 | A | 3/1999 | Deng |
| 6,010,593 | A | 1/2000 | Eymin Petot Tourtollet |
| 6,245,195 | B1 | 6/2001 | Marwah |

FOREIGN PATENT DOCUMENTS

JP 72006202 * 2/1972

OTHER PUBLICATIONS

Ajersch and Pelton, "Mechanisms of Pulp Loss in Flotation Deinking," J. Pulp and Paper Sci. 22, 9:J338-345, Sep. 1996.
Lemlich, R., "A Theory for the Limiting Conductivity of Polyhedral Foam at Low Density," J. Colloid Interface Sci., 64:107 (1978).
Dorris, G., and Page, M., "Deinking of Toner-Printed Papers. Part I: Flotation Kinetics, Froth Stability and Fiber Entrainment," J. Pulp Paper Sci. 23(5), J206-215, May 1997.

(Continued)

*Primary Examiner*—Mark Halpern
(74) *Attorney, Agent, or Firm*—John D. Fado; Lesley E. Shaw; Janet I. Stockhausen

(57) ABSTRACT

A method and apparatus are presented for determining the quantity of liquid and solid content in a removal stream of a froth created from a suspension that is generated during a froth flotation operation. Specifically, electrodes are immersed in the froth generated from a suspension having a known quantity of fiber particles, and the conductance of the froth is measured to establish a relationship between the measured conductance and the quantity of fiber particles. The electrodes are then submerged in a froth generated from a suspension having an unknown quantity of fiber particles, and the froth conductance is measured. The quantity of fiber particles in the froth can then be determined from the pre-established relationship between conductance and solid particle content.

7 Claims, 8 Drawing Sheets

OTHER PUBLICATIONS

Deng and Abazeri, "True Flotation and Physical Entrainment: The Mechanism of Fiber Loss in Flotation Deinking," Nordic Pulp Paper Res. J., 13(1):4, Jan. 1998.

Ajersch, M., Pelton, R., Loewen, S., and Chan, A., "Measurement of Dispersed Air in Newsprint Pulp Suspensions," Tappi J. 75(2):J125-129, Feb. 1992.

Zhu, J.Y.; Wu, G.H.; Deng, Y., "Flotation Deinking of Toner-Printed Papers Using Froth Agent Spray," J. Pulp Paper Sci., 24(9): 295 (1998), Sep. 1996.

Phelan, R., Weaire, D., and Peters, E.A.J., and Verbist, G., "The conductivity of a Foam," J. Phys: Condens. Matter, 8:L475, Jul. 1996.

Weaire, D., Pittet, N., and Hutzler, S., "Steady-State Drainage of an Aqueous Foam", Phys. Rev. Let., 71(16):2670, Oct. 1993.

* cited by examiner

TX-100 = 5–50 mg/L
FIBER CONSISTENCY = 0.5%
FLOTATION TIME = 210s
—— y=1.141*exp(-0.179*x), r²=0.989

■ TX-100 = 5-50 mg/L
FIBER CONSISTENCY = 0.5%
FLOTATION TIME = 210s

METHOD AND APPARATUS FOR MONITORING LIQUID AND SOLID CONTENTS IN A FROTH

CROSS-REFERENCE TO RELATED APPLICATIONS

--

STATEMENT REGARDING FEDERALLY SPONSORED RESEARCH OR DEVELOPMENT

--

BACKGROUND OF THE INVENTION

The present invention relates generally to a froth flotation deinking (ink removal) process for use in paper recycling and, in particular, relates to a method and apparatus for monitoring the liquid and solid content in a froth as a function of froth conductivity.

The recycling of secondary fibers (for example wastepaper) is of growing importance in the protection of the environment by reducing the amount of solid wastepaper and sludge which is placed into landfills. Wastepaper is the largest contributor of the solid waste landfilled each year. About 52 million tons of wastepaper are currently landfilled and, thus, pollute the environment.

Although the paper recycling rate has increased in recent years, the quality of various grades of paper made from recycled wastepaper fibers is far poorer than the quality of similar grades of paper made with virgin (not recycled) paper fibers. Further, the cost of making paper from recycled paper fibers is significantly greater than the cost of making paper from virgin paper fibers.

The objective of paper recycling is to recover paper fibers from the wastepaper, such as photocopied documents or newspapers, which may contain ash, various chemicals, printed or copied inks (offset ink, copying toner particles, etc.) and/or other contaminants.

Froth flotation is an important technique used in the recycling of wastepaper for removing contaminants, such as ink, from the wastepaper. Froth flotation employs the principles of colloid chemistry and physics to separate floatable (hydrophobic) and non-floatable (hydrophilic) particles from each other in an aqueous slurry containing such materials based upon differences in the hydrophobicity of the materials.

Generally, a slurry made from the materials to be separated and water is mixed with 1) a dispersant that separates ink particles from the surface of wastepaper or wood fibers and to prevent the redeposition of separated ink particles on the fibers, 2) a collector that agglomerates small particles to large ones, and changes the surface of hydrophilic ink particles to hydrophobic, and 3) a frothing agent that generates a layer of foam at the upper portion of the froth flotation device for the removal of ink particles and other contaminants. A collector can also be added that causes a surface energy change between solid-liquid, solid-gas, and gas-liquid interfaces.

The mixture is introduced into a froth flotation device, and a pressurized nonreactive gas, such as air, is introduced into the bottom of the device by a generator, and is forced upwards into the slurry in the form of bubbles ranging generally in size from about 50 microns to about 10 cm in diameter. The air bubbles tend to attach to the hydrophobic particles present in the slurry, and cause those particles to rise upwards to the surface of the slurry as a froth layer. The carrying capacity of the bubbles is largely a function of the surface area of the bubbles per unit volume of the froth.

Froth flotation deinking processes thus typically involve three subprocesses: (a) detachment of the ink particles from the wastepaper or wood fibers; (b) adhesion of the ink particles onto air bubble surfaces; and (c) removal of froth and ink particles from flotation cells. The ink particles, many of which are hydrophobic, such as offset ink and copying toner particles, attach to the surface of the air bubbles and float upwards with the bubbles towards the upper portion of a froth flotation device during flotation. Under ideal conditions, the hydrophilic paper fibers will not attach to a hydrophobic air bubble surface. Accordingly, ink removal generally increases with an increase in the rate of froth removal (the rate at which froth is removed from the flotation device), and fiber loss should not occur. As used herein, a reject stream refers to the froth removed from a froth flotation deinking device, as is customary to one having ordinary skill in the art.

Unfortunately, in practice, a significant level of paper fiber loss can occur during froth removal, which mainly results from the physical entrapment (or water carry over) of the fibers in the air bubble network which rises towards the top of the froth flotation device to the froth layer. The mechanisms of pulp loss during froth flotation deinking are described in Ajersch and Pelton, "Mechanisms of Pulp Loss in Flotation Deinking," J. Pulp and Paper Sci. 22, 9:J338-345 (1996). Fiber losses from 4 to 24% by weight have been observed, depending upon the conditions and equipment employed in the froth flotation deinking process. Such fiber loss significantly decreases paper recycling productivity, and correspondingly increases the costs of paper recycling. It is estimated that a 5% increase in the recovery of paper fibers during a froth flotation deinking process will achieve several advantages. First, the increase may significantly increase paper recycling productivity. Additionally, the increase may significantly reduce the costs of paper recycling. Furthermore, the increase may reduce the dry sludge production in a typical paper recycling mill. Accordingly, if a recycling mill has a capacity to recycle 250 tons of wastepaper per day, the recycled output could increase by about 2 tons per day (or 700 tons per year) from the 5% increase. A 10% increase in the paper recycling rate results in a reduction of 8.8 million tons of wastepaper in landfills each year. Even a 1% increase in the paper recycling rate results in a significant reduction of wastepaper in landfills each year.

It should be appreciated that online (real-time) measurement of fiber loss would enable the process control to decrease the entrapment of fibers in the froth. For instance, when a sudden increase of fiber loss is detected, the operator can adjust the flotation conditions to reduce froth stability or reduce the rejection rate momentarily to recover fiber yield. Furthermore, real-time measurement of fiber loss is a prerequisite for implementing any in-process control of fiber yield improvement technologies.

Fiber loss can be measured off-line after flotation deinking by gravimetric methods (i.e., by weighing the oven dry solid of the reject stream to determine the amount of total solid reject), then ashing the solid reject according to TAPPI standard methods to determine the fiber content in the dry solid (unburned materials and other inorganics in the paper are fillers, while the burnt materials are considered to be fiber).

Currently, no systems or methods are in place that are suitable for monitoring the solid content in the removed froth (also referred to herein as a reject stream) in real-time to enable an enhanced control of the dominating factors that affect fiber rejection during a deinking procedure.

What is therefore needed is a method and apparatus for the real-time monitoring of solid content in a reject stream during a froth flotation deinking procedure.

BRIEF SUMMARY OF THE INVENTION

The present invention recognizes that a reliable relationship can be established between the conductance of a froth that contains fiber particles and the quantity of fiber particles. Accordingly, an unknown quantity of solid particles in a froth, created from a suspension during a flotation deinking process, can be determined based on a measured conductance of the froth.

In accordance with one aspect of the present invention, a method is provided for determining a quantity of medium in a froth. The froth is created from a suspension of solid particles in a liquid. The method includes the steps of submerging a pair of spaced electrodes in the froth. Next, the conductance between the electrodes is sensed, and a relationship between the conductance and the quantity of medium is established. Finally, based on the established relationship and the sensed conductance, the quantity of medium in the froth is determined.

In accordance with certain aspects of the invention, the medium is a liquid. In accordance with other aspects of the invention, the medium is a solid.

These and other aspects and advantages of the present invention will appear from the following description. In the description, reference is made to the accompanying drawings which form a part thereof, and in which there is shown by way of illustration, and not limitation, preferred embodiments of the invention. Such embodiments do not necessarily represent the full scope of the invention, and reference should therefore be made to the claims herein for interpreting the scope of the invention.

DETAILED DESCRIPTION OF THE PREFERRED EMBODIMENT

Figure 1:
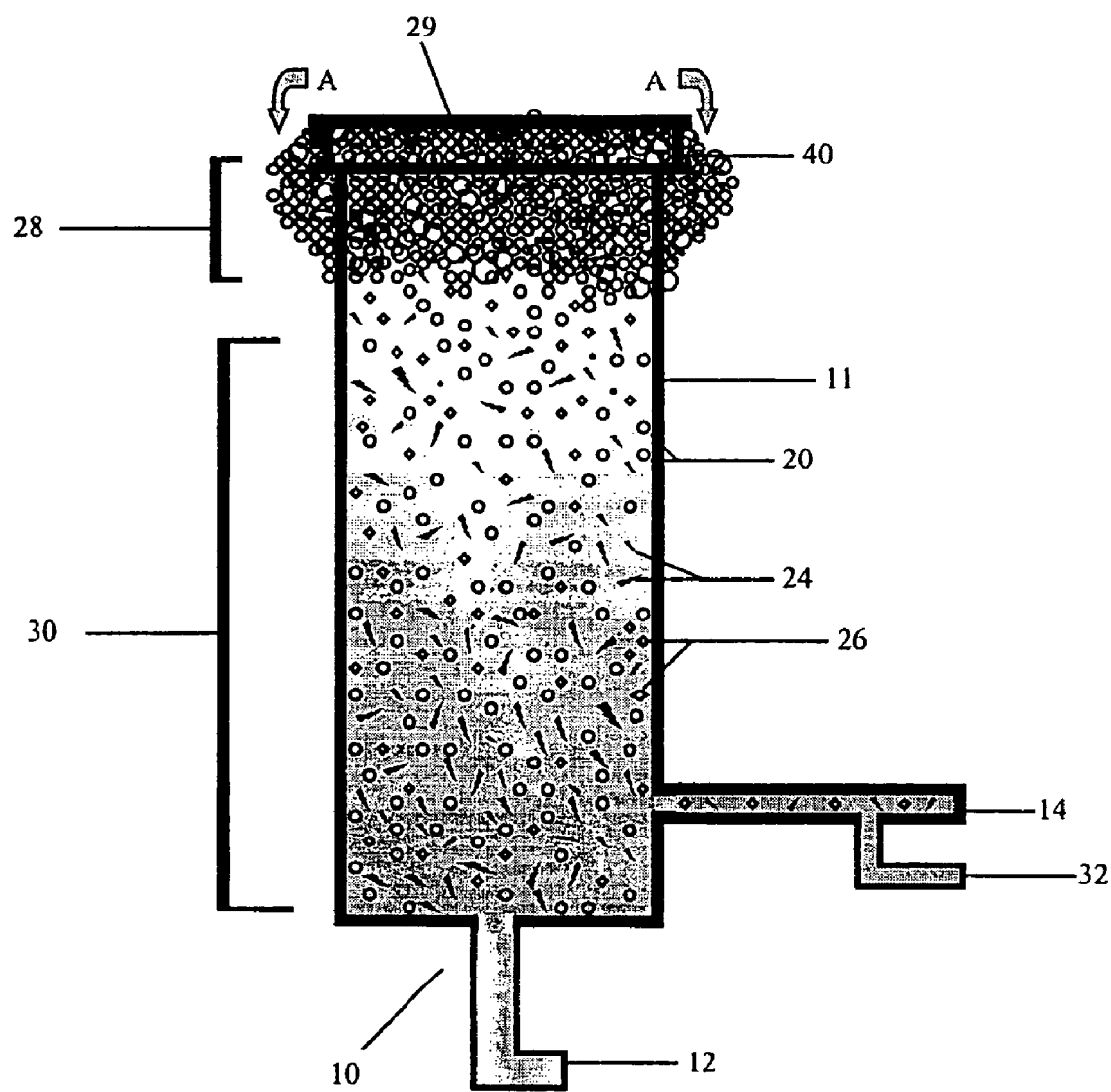
FIG. 1 is a sectional side elevation view of a conductivity probe mounted onto a flotation deinking cell in accordance with one embodiment of the present invention.

Referring to FIG. 1, an exemplary batch-type froth flotation deinking cell 10 includes a housing 11, which can be of a cylindrical, rectangular, or any alternative suitable shape. Housing 11 includes an inlet 14 for the aqueous slurry of wastepaper fibers (pulp suspension), and a column for housing the slurry, or pulp suspension, of wastepaper fibers. The pulp slurry is generally a thin, watery suspension of wastepaper and water made by methods well-known by those of skill in the art. The slurry can contain about 99.5 weight percent of water, and about 0.5 weight percent of paper and/or wood fibers containing ash, ink particles and/or various other contaminants. In other words, the "consistency" of the pulp slurry will be about 0.5%. However, the amount of water present in the pulp slurry is not critical, and may be varied widely. The pulp slurry may be made by, for example, pulping the paper, and mixing the resulting pulp with water.

Housing 11 can also include an inlet 32 that introduces a dispersant, frother, and collector into the pulp suspension. It should be appreciated that all deinking chemicals can be added directly during the pulping process prior to flotation. Alternatively, a liquid solution containing a frothing agent can be mechanically added to the top surface or portion of the wastepaper pulp slurry introduced into a froth flotation deinking device (or to the top surface or portion of the froth layer produced in a froth flotation device) during a froth flotation deinking separation process from above the top surface of the pulp suspension (or froth layer), or from within the top portion of the pulp slurry (or froth layer), as described in U.S. Pat. No. 5,876,558, the disclosure of which is hereby incorporated by reference as if set forth in its entirety herein.

The frothing agent causes a froth layer 29 to form in the upper portion 28 of the cell 10, with the lower portion 30 of the device containing little or no froth. The froth layer 29 contains ink particles and other contaminants 26. Hydrophobic contaminants and ink particles adhere to the surfaces of air bubbles that rise to the top of a flotation cell and are expelled when the froth layer 29 overflow is removed (for example, by known mechanical methods (e.g., vacuum suction of the froth layer)). The froth flotation cell 10 thus separates wood fibers 24 to be recaptured from ink particles and other contaminants 26 to be discarded. As illustrated, the ink and contaminants 26 are expelled when the froth layer 29 overflows from the column.

Cell 10 further includes a gas inlet 12 that produces gaseous bubbles 20 from a pressurized nonreactive gas, such as air, nitrogen, carbon dioxide, helium or the like, that is introduced into the lower portion in a manner known by those of skill in the art. The flow rate of the air or other nonreactive gas being introduced into the froth flotation device will vary, depending upon the capacity of the particular froth flotation column being used, and may readily be determined by a person of skill in the art. For example, for a 6-liter froth flotation column, the flow rate of the nonreactive gas will preferably range from about 10 to about 45 standard liters per minute (slpm). Porous materials, such as screens, nozzles, filters and like devices, with different pore sizes may also be employed to produce bubbles at the lower portion of the froth flotation device.

While an exemplary batch-type froth flotation deinking cell 10 has been illustrated, it should be appreciated that any froth flotation device, such as a batch- or continuous-type column cell, or a rotating deinking cell, or dissolved gas flotation deinking cell, can be used in accordance with the principles of the present invention.

The present invention recognizes Lemlich's expression of a relationship between liquid volumetric fraction in a froth and the conductivity of the froth relative to the suspension conductivity, as set forth below in Equation (1). Leimlich, R., A theory for the limiting conductivity of polyhedral foam at low density, J. Colloid Interface Sci., 64:107 (1978).

$$\sigma_{froth} = \Phi_1/3 \tag{1}$$

where $\sigma_{froth}$ is the conductivity of the froth relative to the liquid conductivity, and $\Phi_1$ is the liquid volumetric fraction in the froth. Equation 1, however, has only been applied to aqueous froths that consists of liquid and gas (i.e., no solid content in the froth).

The present inventors have recognized that the wet rejection rate through froth removal ($R_w$) can be expressed as the product of liquid volumetric fraction and the volumetric rate of froth rejection, or production, ($R_{froth}$). Specifically, $$R_w = \Phi_1 \cdot R_{froth} = 3 \cdot \sigma_{froth} \cdot R_{froth} \tag{2}$$

Equation (2) thus states that the froth conductivity can be related to the wet rejection rate and the volumetric rate of froth rejection. However, the volumetric rate of froth rejection is difficult to measure in industrial practice.

Fiber rejection loss ($R_{fib}$) can be expressed as the wet rejection loss times the fiber consistency ($\chi_{fib}$) in the rejection stream, as follows:

$$R_{fib} = \chi_{fib} \cdot R_w = 3 \cdot \chi_{fib} \cdot \sigma_{froth} \cdot R_{froth} \tag{3}$$

Equation (3) shows that fiber rejection rate can also be related to froth conductivity as hypothesized and to be validated by the present inventors.

In order to monitor wet and fiber rejection in froth flotation, it is desirable to ascertain the froth volumetric rejection (or production) rate and fiber consistency in the rejection stream. The general level of knowledge has been that the operating conditions, in particular the flotation aeration rate and the surfactant and its concentration, affect froth production or rejection rate. Accordingly, $$R_w = 3 \cdot \sigma_{froth} \cdot R_{froth} \alpha \sigma_{froth} \cdot f(\text{operating conditions}) \tag{4}$$

where $f$(operating conditions) is an empirically derived function based on the operating conditions during the froth flotation deinking process, and "$\alpha$" is a proportional symbol.

For a given fiber consistency of the suspension under flotation, the fiber consistency in the reject stream is primarily affected by the drainage of liquid (water) and fiber to some extent through the plateau border (PB) channels formed by the films on the faces of the polyhedral bubbles in the froth, which are functions of the froth structure that is also dictated by the flotation operating conditions (Zhu and Tan, Canadian J. Chemical Eng., in press, 2005).

Equations (1) and (4) are known to hold true for liquid froths that do not contain fiber or any other solids. The present inventors recognizes that if Equations (1) and (4) are also true for solid-containing froths, then the fiber consistency in a froth can be measured by froth conductivity. Specifically, $$\chi_{fib} \alpha g(\sigma_{froth}) \tag{5}$$

where $g(\sigma_{froth})$ is recognized by the present invention as a function that can be used to establish a relationship between fiber content in a froth reject stream and the conductance of the froth, and $\sigma_{froth}$ is the froth conductivity.

Substituting equations (4) and (5) into equation (3), $$R_{fib} = \chi_{fib} \cdot R_w \alpha G(\sigma_{froth}) \cdot F(\text{operating conditions}) \tag{6}$$

The present invention thus recognizes that a medium (specifically, wet (or liquid) and fiber (or solid) rejection) in a froth flotation device can be determined and monitored based on froth conductivity, provided that the froth conductivity does indeed provide an accurate measurement of liquid volumetric fraction (and hence the quantity of solids in the froth) even when the froth contains solid particles as hypothesized by the present inventors. If the froth conductivity provides an accurate measurement of liquid volumetric fraction, then the calibration functions "g" and "f" can be determined empirically through experiments according to Equations (4) and (6) for the determination of wet and fiber content and rejection in froth flotation of fiber suspensions.

Figure 2:
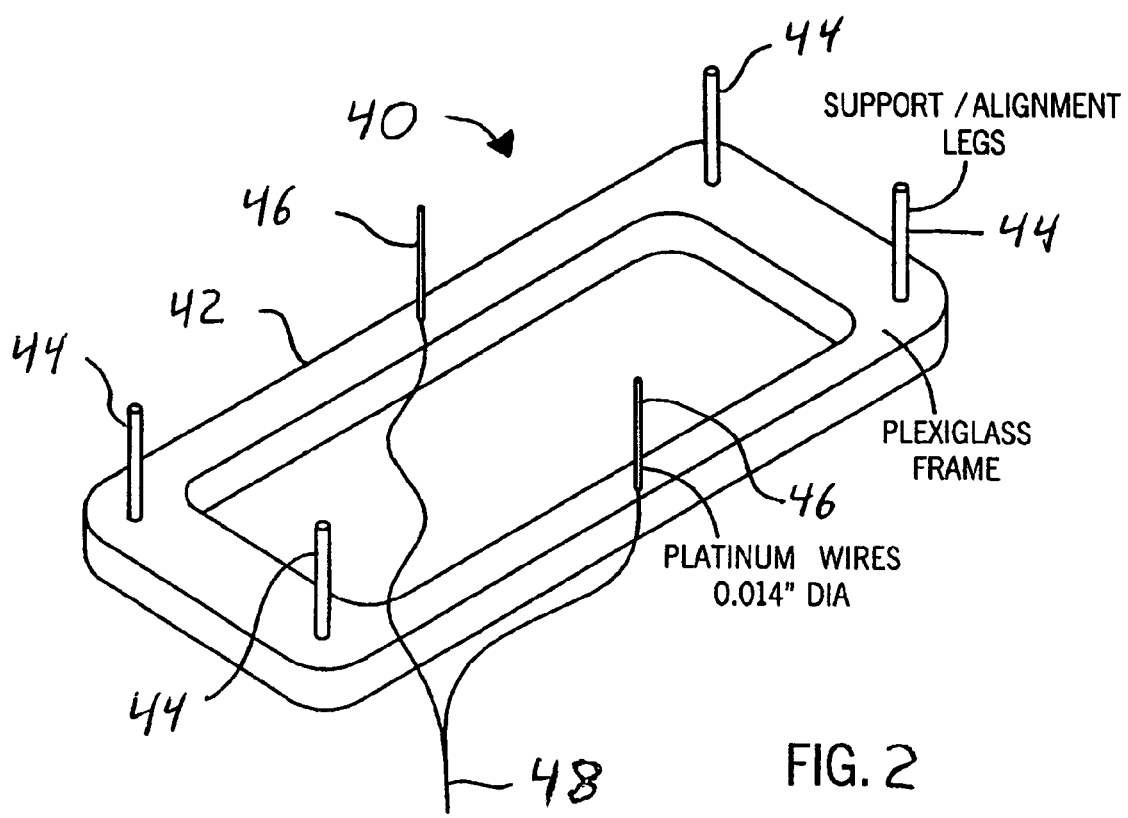
FIG. 2 is a perspective view of the conductivity probe illustrated in FIG. 1.

Accordingly, referring to FIGS. 1 and 2, a froth conductivity probe 40 includes a mounting frame 42 which can, for example, be made of an acrylic. Frame 42 supports a pair of sensing electrodes 46 which, for example, can comprise platinum wires. Frame 42 has a hollow interior to enable the froth 29 to rise through the probe 40 when desired. Four legs 44, which can comprise brass, are mounted in the corners of frame 42 and both support and align the probe 40 relative to the flotation column. The conductivity probe 40 can thus be mounted onto the open end of the column with the legs 44 extending downwardly proximal the column to fix the position of the probe 40 relative to the column. The sensing electrodes 46 extend downward into the froth 29. Signal extension wires 48 can be clamped or otherwise fastened to the sensing electrodes 46 in the frame 42. During operation, the froth to be removed (reject stream) travels vertically driven by aeration through the frame 42 and overflows along the direction of Arrows A (FIG. 1).

In the Examples below, the probe 40 was connected to a conductance meter (i.e., Model 35, Yellow Springs Instrument Co., located in Yellow Spring, Ohio, that applies a voltage from one electrode 46 to the other. Based on the sensed voltage at the other electrode 46 and the known distance between the electrodes 46, the conductivity can be determined. A data logger (Model IQVma, Measurement Computing, located in Middleboro, Mass.), was connected to the analog output of the conductance meter for recording the conductance readings. The probe 40 measured the conductance of the froth with a length of approximately 1.25 in. (i.e., the length of the electrodes 46) and a distance between the electrodes 46 of approximately 2.75 in.

Figure 4:
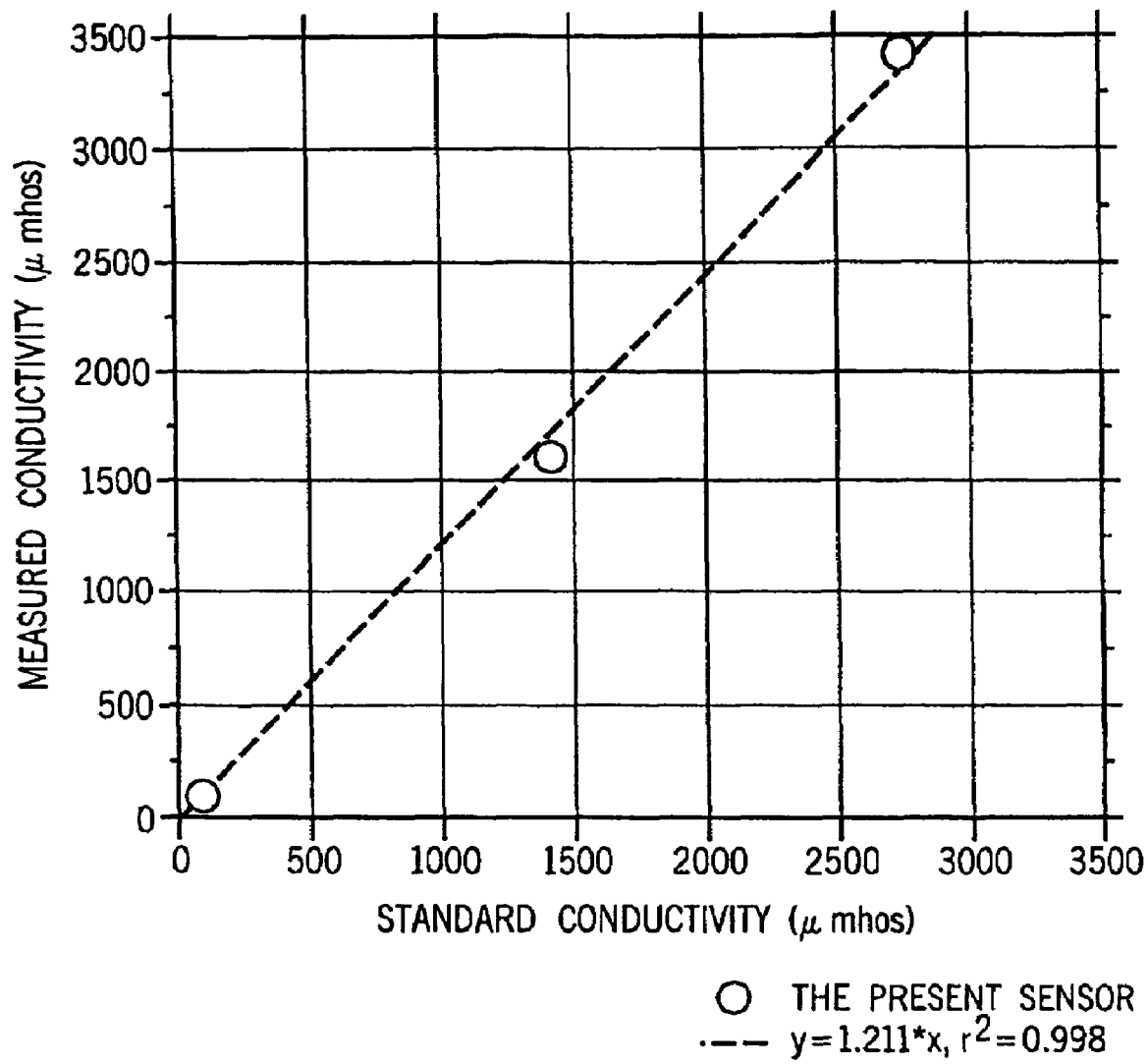
FIG. 4 is a graph illustrating a probe-measured liquid conductivity as a function of a known liquid conductivity to establish a reliability of probe measurement.

First, however, the reliability of the probe was verified as illustrated in FIG. 4. Specifically, the graph of FIG. 4 plots conductivities of the standards against measured conductivity. FIG. 4 exhibited a highly linear response, thus indicating a high reliability of the present conductivity probe 40.

It should be appreciated that when the probe 40 is applied to a foam, or froth, the measured conductivity represents the average conductivity of the medium within the described dimension, which correlates to the volumetric liquid fraction of the foam according to Lemlich's Equation 1. (As used herein, the term "foam" relates to a stagnant mass while a "froth" refers to a mass that moves within the deinking cell.) This is because the conductive liquid that is disposed in the void spaces in the gaseous bubble network contributes to the conductivity of the froth. It should thus be appreciated that a dry foam is less conductive than a wet foam (which contains more conductive liquid). Accordingly, different probe designs can be implemented for different applications.

Figure 3:
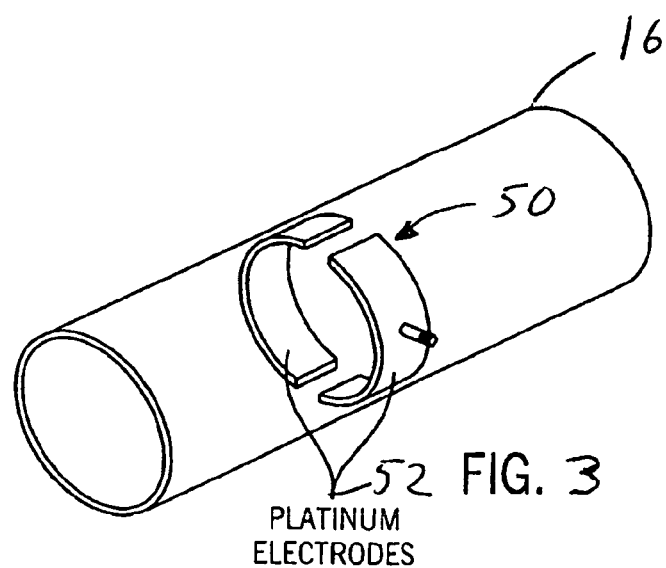
FIG. 3 is a perspective view of a conductivity probe integrated into a froth reject stream in accordance with an alternative embodiment.

For instance, referring to FIG. 3, a froth conductivity probe 50 constructed in accordance with an alternative embodiment of the invention is shown integrated into a reject stream of the type described above (illustrated schematically in FIG. 3). Specifically, two arc-shaped electrode bands provide the electrodes 52 and are mounted onto the inner surface of a pipe of the rejection stream.

Example 1

A first laboratory experiment was conducted using a suspension of nylon fiber in a column air flotation cell. The nylon fibers had a length of approximately 3 mm and a diameter of 15 denier (43.2 µm) and were obtained from Minifibers, Inc., located in Johnson City, Tenn. The flotation column is made of acrylic glass having an inner diameter of 6.25 in. and a length of 42 in. A circular stainless steel porous disk having a thickness of 0.25 in. and a diameter of 6.25 in. was mounted at the bottom of the column for aeration. The disk used is commercially available from Sinter Metals Filters, GmbHm, located in Germany, as Model SIKA-R 200. The porosity of the disk was 51%, and the disk had a minimum pore diameter of 28 µm, a maximum pore diameter of 135 µm, and an effective pore diameter of 65 µm, which produces an equivalent diameter of 70 µm. Readily available pressurized air was used to achieve flotation. A pressure regulator and flowmeter, commercially available from OMEGA, located in Stamford, Conn. under Model FMA-A2317, was used to regulate the air flow rate. A check valve was installed in the air flow line to prevent back flow of water to the flowmeter.

The majority of the flotation trials were conducted with a fiber consistency of 0.5% in the suspension (though fiber consistency was doubled and tripled in some instances to evaluate the effect of fiber consistency). The suspension level was varied between 1.5 in. and 0.5 in. from the top of the column. The air flow rate was varied from 5-50 L/min. Triton X-100 "(a nonionic octyl phenyl oxyethylenic surfactant) analytical grade, commercially available from Advance Scientific and Chemical Inc., located in Fort Lauderdale, Fla., was used as the surfactant, whose concentration was varied from 50-200 mg/L in the suspension. Potassium chloride (1.2 grams) was added to the fiber suspension to increase the conductivity, thus improving conductivity measurement sensitivity (raised the conductivity of the suspension to ~650 µmhos).

In order to determine the correlation between froth conductivity and the liquid volumetric fraction in the froth, the measured froth conductivity must be a good representation of the froth that is analyzed for volumetric liquid fraction determination. Accordingly, the volume of froth should therefore be collected in real-time during conductivity measurements.

Accordingly, a 1.75 in. tall cylindrical collection collar (of the type described above for the flotation cell) was placed on top of the flotation cell during experiments, and was used to collect froth. The bottom of the collection collar was connected with a rubber ring using silicone glue to prevent water leakage during froth collection and flotation. A circular aluminum disk of approximately 8 in. diameter was used to collect the froth when the collar was removed.

When the surfactant was applied, froth arose with the air flotation and gradually filled the collar after the start of aeration. The filling rate is dependent upon the air flow rate, the surfactant, and the surfactant concentration. A timer was used to record the filling time. During the froth filling period, the conductivity probe 40 was mounted in the manner illustrated in FIG. 1. Accordingly, the electrodes 46 were submerged in the froth to be collected, and the measured conductivity was an accurate measure of the collected froth. Once the collection collar became completely filled with froth, the aluminum disk was inserted into the joint location between the collar and the flotation cell to collect the froth. The froth was then weighed, and the conductivity of the froth was recorded. The volumetric liquid fraction in the froth could thus be calculated from the volume of the collar and the mass of water in the collected froth.

Figure 5:
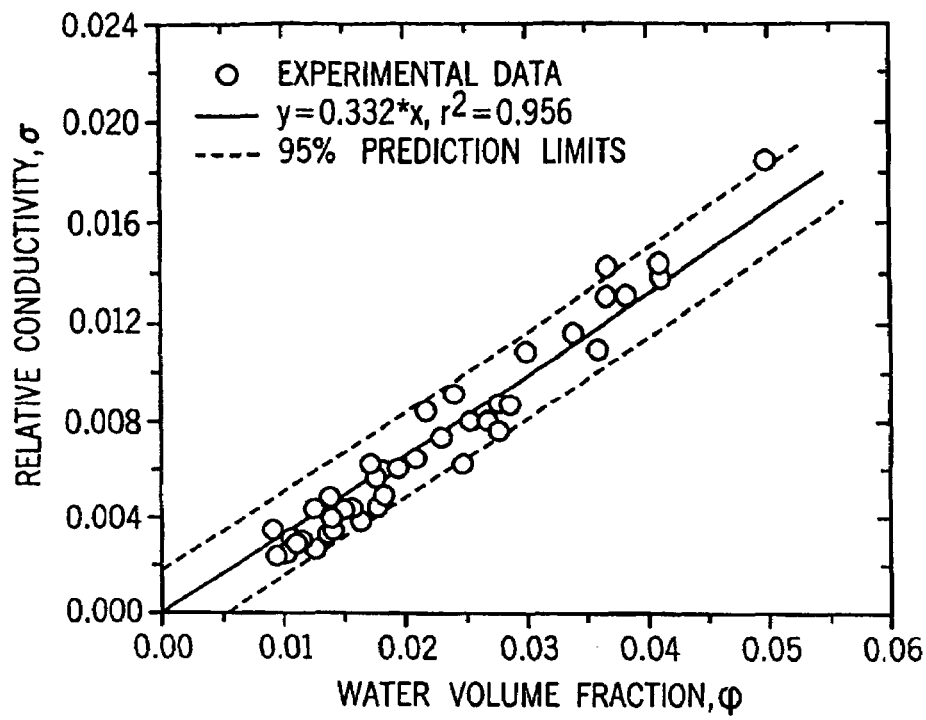
FIG. 5 is a graph plotting conductivity of the froth (relative to the conductivity of a particle suspension) as a function of the water volumetric fraction in the froth.

The results of the experiment are illustrated in FIG. 5, which plots conductivity of the froth (relative to the conductivity of the fiber suspension) against the measured water volumetric fraction. The data was obtained from forty-eight different trials conducted under a wide range of air flowrates, surfactant concentrations, fiber consistency, initial suspension of water levels, and over a period of about two weeks. As illustrated, the data scatter is not significant, and the data follows the universal trend that the relative conductivity of the froth is linearly proportional to the volumetric water fraction within the froth. Furthermore, a linear regression analysis indicates that the proportionality constant is equal to 0.332 with an $r^2$ value of 0.956. The 0.332 proportionality constant is only about 0.4% less than the theoretical value in the Lemlich Equation (1).

The results depicted in FIG. 5 indicate that Lemlich's relation between froth conductivity and liquid volumetric fraction in a froth is also valid for froth containing fiber suspensions.

Example 2

An additional set of trials was conducted to determine the relationship between water reject (liquid) and oven dry (OD) fiber reject (solid) through froth removal during air flotation, or the fiber consistency in the reject stream. For these trials, it was recognized that the collection collar weighs three orders of magnitude greater than the fiber mass in the collected reject stream, and the collection collar was accordingly not used. Instead, the conductivity probe 40 was held in position directly above the column air flotation cell, with the distal ends of the electrodes 46 level with the top of the column.

Once aeration commenced, the froth began rising above the water level and, as it flowed upward and out of the flotation column, the froth retained a cylindrical shape with minimal deformation. Once the electrode was completely submerged in froth above the column, the conductivity reading was recorded and the exposed froth was scraped onto an aluminum foil collector. Advantageously, the collector weight was only one order of magnitude larger than the weight of the fiber in the collected froth. A number of identical froth collections commenced under a fixed set of conditions (e.g., same air flow rate, surfactant concentration, fiber consistency, etc . . . ) without interruption of aeration.

The conductivity reading obtained in the first collection was used as a basis to start collection for the subsequent froth collections. A timer was used to determine the time required for both the froth to rise from the suspension surface to the flotation top end and the time of collection. The volume of the froth collected was approximately equal to the volume of a cylinder of 1.25 in. long (the length of the electrodes 46). A new collector was used in each collection and the weight of the collector was first measured for a gravimetric determination of water and fiber rejection. The wet rejects in the collector were weighed and put in an oven at 105° C. to determine the OD fiber mass in the collected froth. The collector was dried overnight, removed, and weighed after cooling.

Before beginning flotation under a new set of operating conditions, forced air was used to completely destroy the froth. Furthermore, the suspension was thoroughly stirred to obtain a uniform fiber suspension.

Previous research has indicated that the quantity of solid rejects is linearly proportional to the quantity of wet reject through froth removal in air flotation (see, for instance, Ajersch and Pelton, Mechanisms of Pulp Loss in Flotation Deinking, J. Pulp and Paper Sci. 22, 9:J338-345 (1996); and Deng and Abazeri, True Flotation and Physical Entrainment: The Mechanism of Fiber Loss in Flotation Deinking, Nordic Pulp Paper Res. J., 13(1):4, 1998.) The present inventors recognize that a proportional coefficient of the relationship between fiber and wet reject is essentially the time-averaged fiber consistency of the wet reject stream. Accordingly, in FIG. 6, the accumulative fiber reject (OD) is plotted as a function of the accumulative wet reject from the data obtained in the above-described identical froth collections conducted under fixed flotation conditions. The slope of each plot is therefore the fiber consistency in the reject stream.

Figure 6:
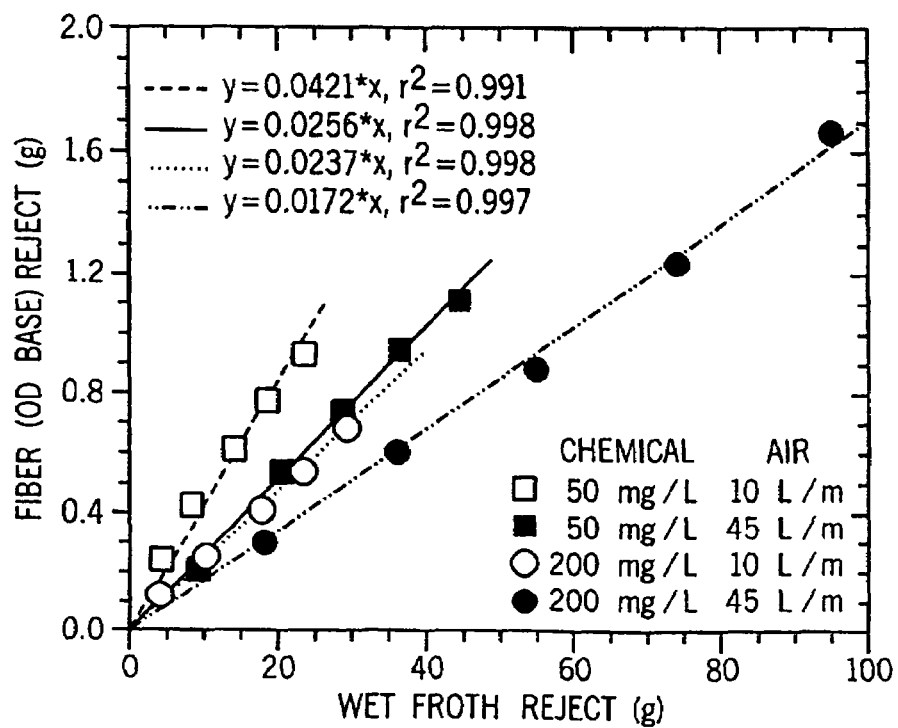
FIG. 6 is a graph plotting fiber reject as a function of wet froth reject for a plurality of tests using different surfactant applications and aeration rates.

It is appreciated that excellent linear correlations (i.e., correlation coefficients greater than 0.99) were obtained between the total liquid reject and the fiber reject in FIG. 6. FIG. 6 thus clearly illustrates that the fiber consistency in the rejected stream varies with the surfactant chemical charge and aeration flow rate in flotation. Furthermore, the zero "y-intercept" indicates that the fibers were rejected through entrainment rather than to adhering to air bubbles in the froth, according to Ajersch and Pelton, Mechanisms of Pulp Loss in Flotation Deinking, J. Pulp and Paper Sci. 22, 9:J338-345 (1996). FIG. 6 also indicates that increasing surfactant charge or aeration reduces the fiber consistency in the rejection stream.

Figure 7:
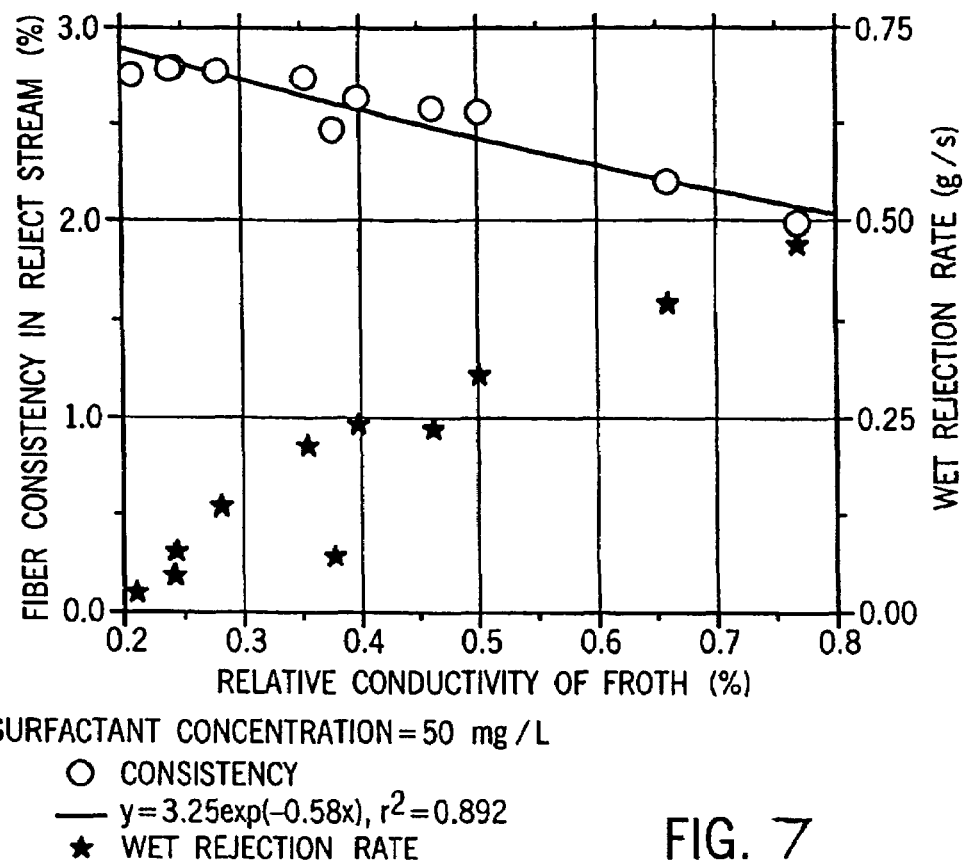
FIG. 7 is a graph plotting fiber consistency and wet rejection rate both as a function of the relative froth conductivity for varying air flow rates.

Additional trials were conducted while varying the air-flow rate from 6.6-24.0 L/min (with a fixed TX-100 surfactant concentration of 50 mg/L) to determine the effect of air flowrate on the fiber consistency in the rejected stream. The fiber consistency in the reject stream obtained using linear regression as illustrated by FIG. 6 was plotted against the conductivity of the rejected froth, relative to the suspension conductivity, in FIG. 7. As illustrated, the fiber consistency in the suspension decreases exponentially with increasing measured froth conductivity. The data illustrated in FIG. 7 was collected on three different days spanning two weeks, thus indicating the repeatability of the experiments. FIG. 7 also demonstrates that the conductivity can indeed be used to monitor fiber consistency in the reject stream of froth flotation (i.e., the function "g" in Equation 5 can be approximated by an exponential decay function).

FIG. 7 also indicates that Lemlich's Equation (1), which identifies a relationship between liquid volumetric fraction in an aqueous froth, can be used as the basis to measure wet rejection rate even when the froth contains solid particles or fibers.

Figure 8:
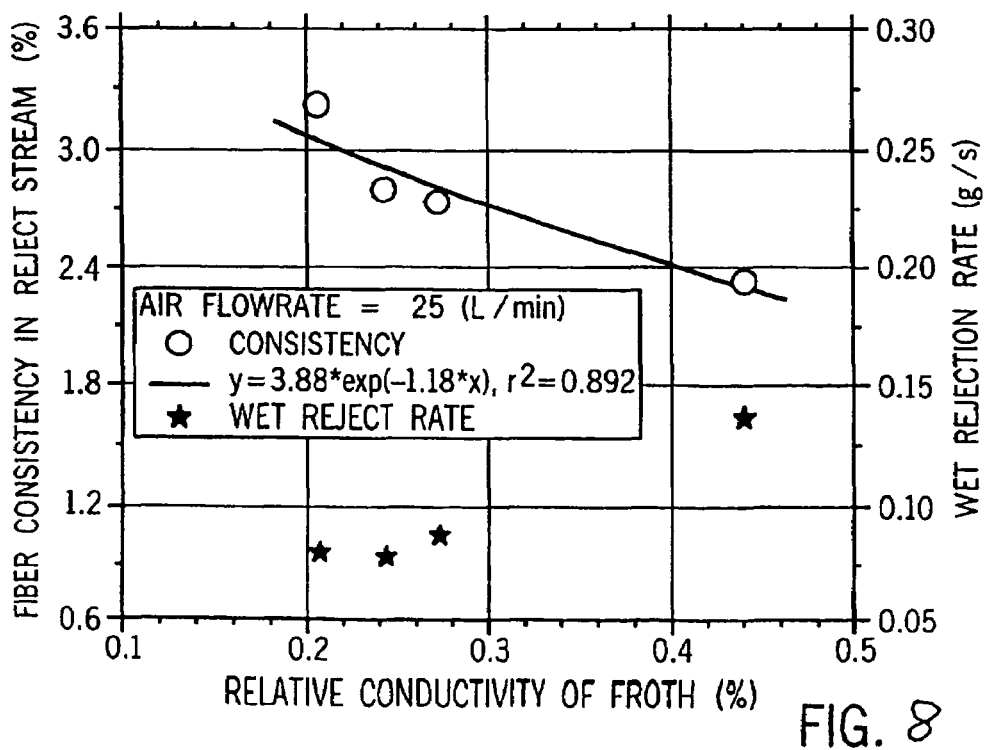
FIG. 8 is a graph plotting fiber consistency and wet rejection rate as a function of the relative froth conductivity for varying surfactant concentrations.

Yet another set of trials was conducted while varying the surfactant concentration (i.e., 25, 50, 100, and 200 mg/L) in the suspension while maintaining a fixed air flowrate of 25 L/m to determine the effect of surfactant concentration in the suspension on fiber consistency in the reject stream. A regression was performed on the data of fiber consistency in the reject stream plotted against the conductivity of the rejected froth relative to the suspension conductivity. As illustrated in FIG. 8, it was found again that the fiber consistency in the reject stream decreased exponentially with increasing froth conductivity, indicating the function "g" in Equation 5 can be approximated by an exponential decay function. The parameters in the fitted exponential decay expression are different from those of FIG. 7 because the surfactant concentration affects fiber rejection loss differently than aeration affects fiber rejection loss.

Figure 9:
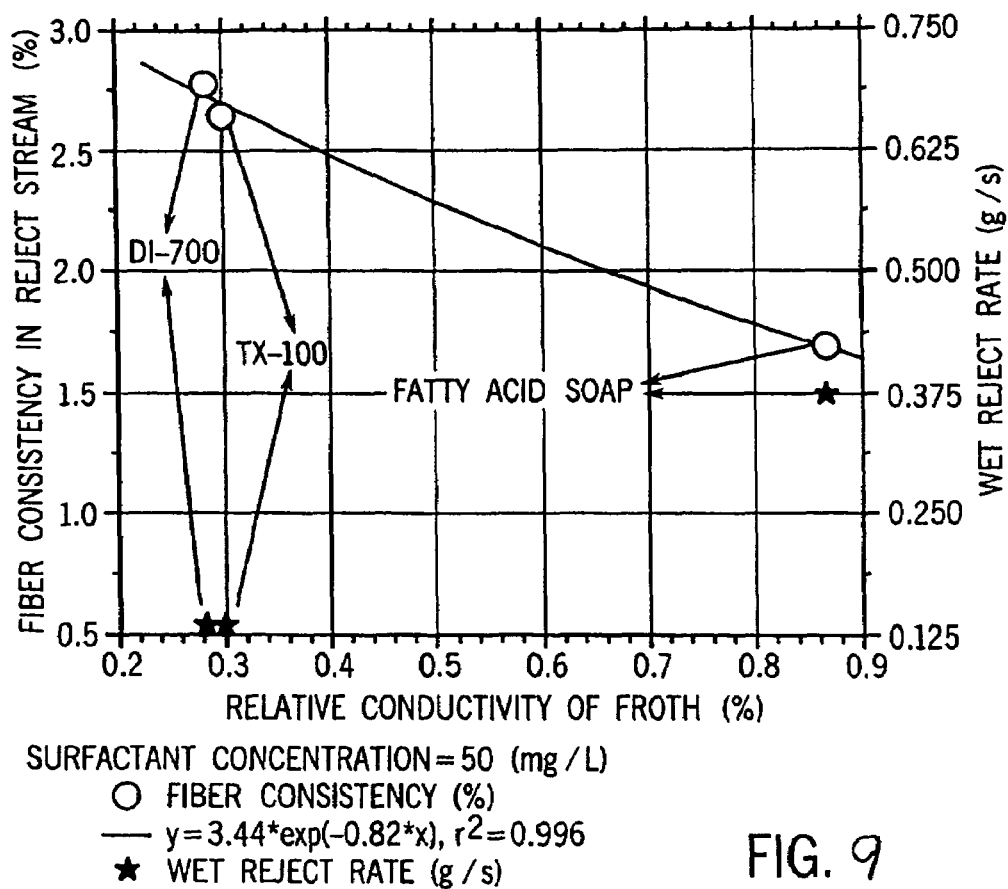
FIG. 9 is a graph plotting fiber consistency and wet rejection rate as a function of the relative froth conductivity for a plurality of surfactants.

Another set of trials was conducted that varied the surfactants used in the suspension to determine the effect of the various surfactants on fiber consistency in the rejection stream. The results, illustrated in FIG. 9, indicate that different surfactants affect fiber rejection loss differently.

Figure 10:
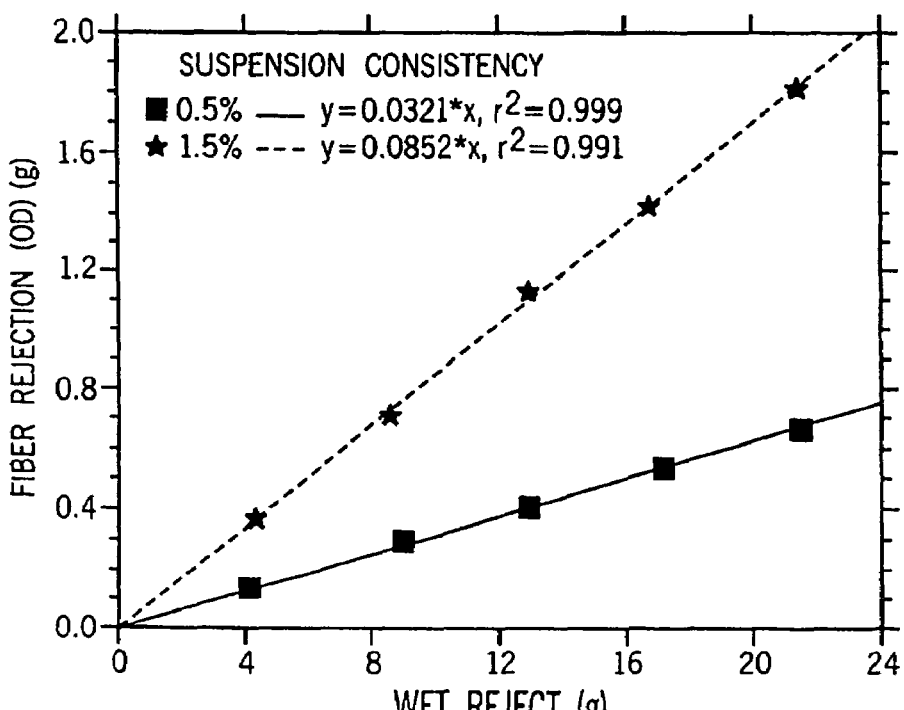
FIG. 10 is a graph plotting the amount of fiber rejection as a function of the amount of wet rejection under conditions of varying fiber consistencies.

Still another set of trials was conducted that varied the fiber consistency in the suspension to determine its effect on the fiber concentration in the froth reject stream. FIG. 10 illustrates that increasing the fiber consistency in the suspension increases the fiber consistency in the reject stream. It appears, based on the results of the trials, that fiber consistency in the reject stream (i.e., the slope of the linear regression lines of FIG. 10) is linearly proportional to the fiber consistency of the suspension.

Example 3

A series of experiments was conducted to further demonstrate the ability to reliably determine fiber content in the reject stream of a flotation deinking process by measuring conductivity of the froth using a probe constructed in accordance with the principles of the present invention. The trials were conducted using an 8-liter Denver flotation cell, available from Denver Equipment Company, located in Colorado Springs, Colo., as appreciated by one having ordinary skill in the art. Partially deinked secondary fibers consisting of old newsprint from Madison Newsprint Company, located in Madison, Wis. and old magazine obtained from Quad Graphics, Sussex, Wis. with a mix ratio of 9:1, respectively, were used to create a fiber suspension of 0.5% consistency. The fiber was obtained from the accept stream of previous flotation deinking trials. The conductivity probe was placed such that the electrodes were vertically oriented into the froth during flotation, with the distal ends of the electrodes spaced approximately 1 cm above the suspension level in the Denver cell to keep the electrodes from directly contacting the suspension during flotation when the water level was raised by aeration. The addition of surfactant cause the froth to rise and completely submerge the conductivity probe.

Figure 11:
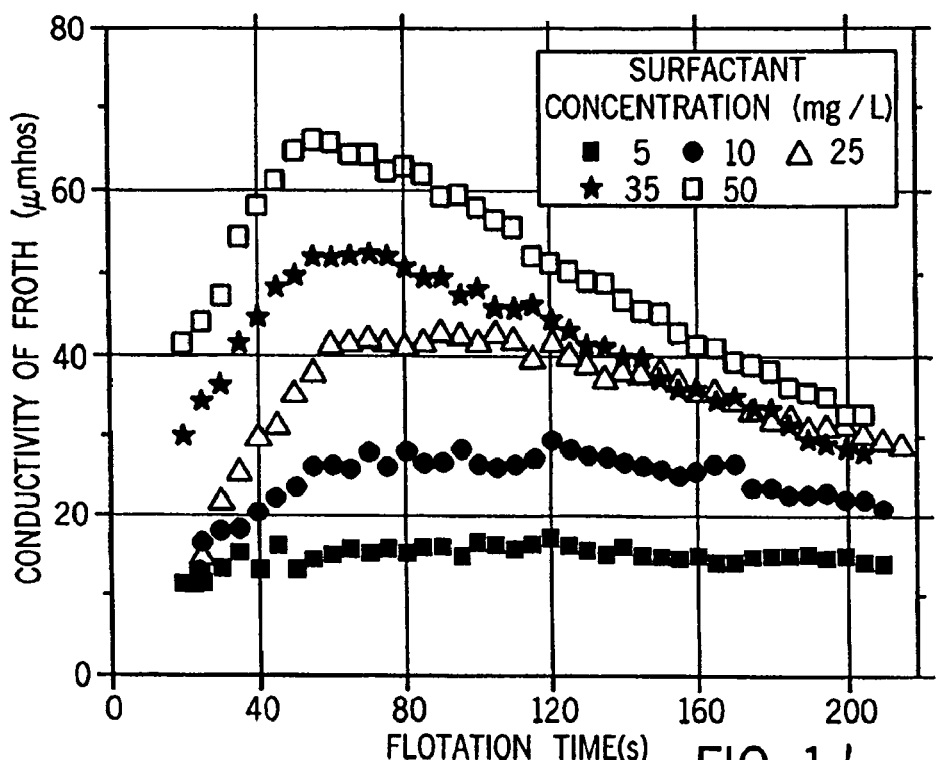
FIG. 11 is a graph plotting froth conductivity as a function of time for a plurality of surfactant concentrations.

The froth conductivity was recorded at a frequency of 0.25 Hz using a personal computer. During the first 210 seconds of flotation, the water level rose initially by aeration and then decreased due to wet rejection. FIG. 11 illustrates the measured froth conductivity as a function of time using various surfactant concentrations. The conductivity data of the first 20 seconds were not reported due to the transient behavior experienced during start-up. In FIG. 11, the variation of the measured conductivity was not significant over time at low surfactant concentrations that resulted in low froth stability and therefore low gas hold up, low water content, and less wet rejection.

Figure 12:
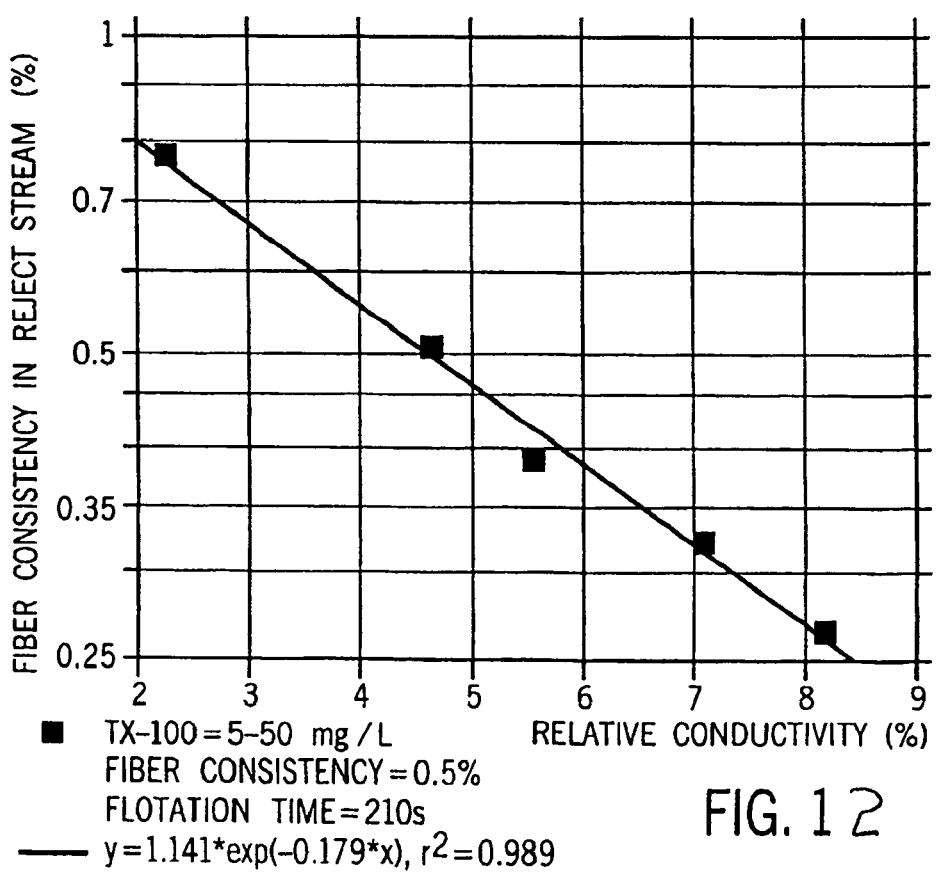
FIG. 12 is a calibration curve plotting fiber consistency in the reject stream as a function of the relative conductivity of the froth.

The reject stream was collected and analyzed for total weight and solids (primarily fiber but also small amounts of ash, including filler and ink). The ash content of the feed deinking pulp stock was about 5% by mass. The time-averaged conductivity over the first 210 seconds was used to represent the froth conductivity during the entire flotation period. As illustrated in FIG. 12, the fiber consistency in the reject stream decreases exponentially with the increase of average conductivity of the froth relative to the suspension conductivity. The exponential decay function fits the conductivity data quite well, with a correlation coefficient of about 0.99, which again demonstrates that the function "g" in Equation 5 can be approximated by an exponential decay function. Similar results were obtained when a different deinking surfactant was used.

Figure 13:
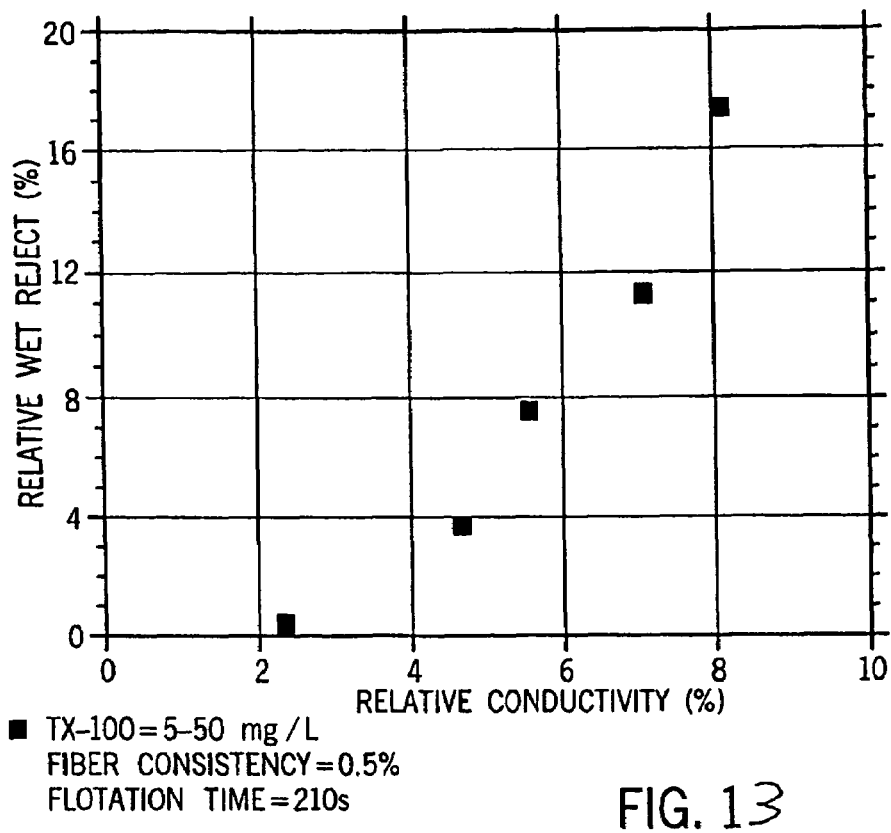
FIG. 13 is a calibration curve plotting the relative wet reject percentage (equal to the wet reject divided by the total suspension weight in the flotation cell) as a function of the average froth conductivity (relative to the conductivity of the suspension) for varying surfactant concentrations.
Figure 14:
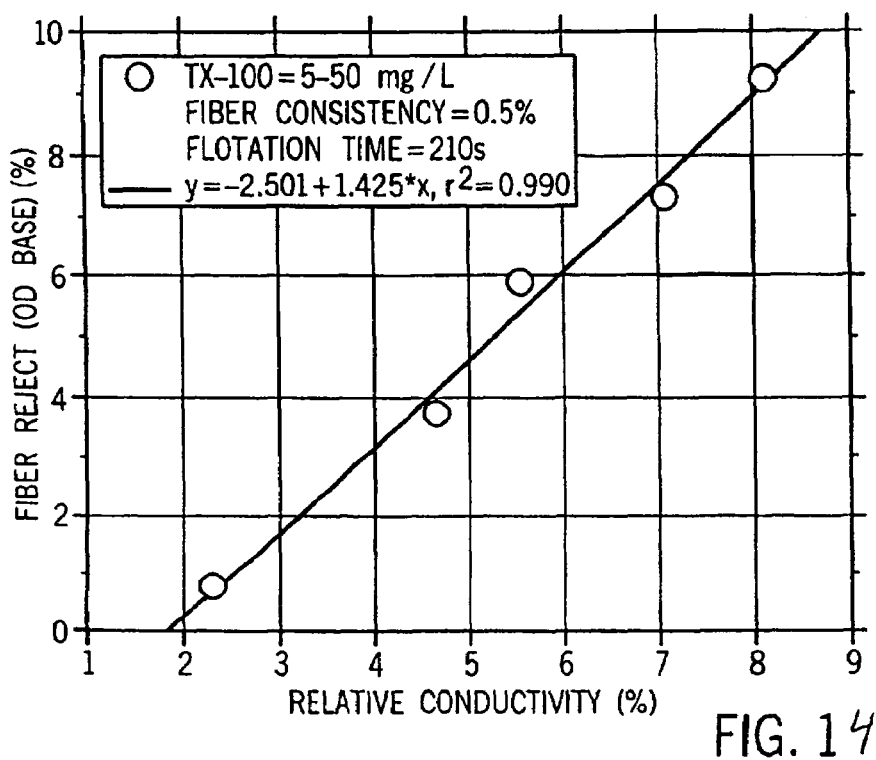
FIG. 14 is a calibration curve plotting the fiber rejection loss as a function of froth conductivity relative to the conductivity of the suspension.

Referring to FIG. 13, it was found that the measured conductivity also correlated quite well to the relative wet rejection fraction (equal to the wet reject divided by the total suspension weight in the flotation cell). FIG. 14 clearly shows that the fiber rejection loss is linearly proportional to the measured froth conductivity with a correlation coefficient of 0.99.

These examples demonstrate that the total fiber rejects (i.e., the product of fiber consistency in the reject stream and the total wet rejects) can also be determined based on the conductivity data of a solid-containing froth. As a result, the fiber consistency of a reject stream, the total wet reject, and the total fiber reject can be monitored by measuring conductivity of the froth during flotation deinking.

The present invention has been described in connection with what are presently considered to be the most practical and preferred embodiments. However, the present invention has been presented by way of illustration and is not intended to be limited to the disclosed embodiments. For instance, the principles of the present invention are equally applicable to froth flotation mineral removal processes in which mineral solids are removed in a froth (the removed froth is considered to be an "accepted stream" as opposed to the deinking process in which the removed froth is considered as the reject stream). Accordingly, those skilled in the art will realize that the invention is intended to encompass all modifications and alternative arrangements included within the spirit and scope of the invention, as set forth by the appended claims.

We claim:

1. A froth flotation device comprising:
   a housing having at least one inlet for delivery of a suspension, the housing having an interior space for retaining the suspension, the suspension including a frothing agent and a gas, wherein the frothing agent and gas in combination generate a froth from the suspension; and
   a sensor that measures a quantity of a medium in the froth, the sensor including a pair of electrodes disposed at a level above the upper end of the housing and spaced a known distance apart, wherein the froth is raised to a height such that the electrodes are immersed in the froth and the electrodes measure a conductance level of the froth to determine the quantity of the medium in the froth based on a pre-established relationship between the measured froth conductance level and a quantity of fiber in the froth.

2. The froth flotation device as recited in claim 1, wherein the medium is selected from the group consisting of liquid and solid particles.

3. The froth flotation device as recited in claim 2, wherein the solid particles comprise a fibrous content.

4. The froth flotation device as recited in claim 3, wherein the fibrous solid content is generated from a pulp suspension.

5. The froth flotation device as recited in claim 1, wherein a voltage is applied across the electrodes.

6. The froth flotation device as recited in claim 1, wherein at least a portion of the froth is removed from the froth flotation device as a froth removal stream.

7. The froth flotation device as recited in claim 1, further comprising a gas source emitting the gas into the suspension.

* * * * *